United States Patent
Kindaichi et al.

(10) Patent No.: US 9,072,622 B2
(45) Date of Patent: *Jul. 7, 2015

(54) COATING METHOD AND COATING APPARATUS

(71) Applicant: Terumo Kabushiki Kaisha, Shibuya-ku (JP)

(72) Inventors: Shori Kindaichi, Shizuoka (JP); Yasukazu Harada, Shizuoka (JP); Kazuyuki Takeda, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/199,648

(22) Filed: Mar. 6, 2014

(65) Prior Publication Data

US 2014/0186516 A1 Jul. 3, 2014

Related U.S. Application Data

(63) Continuation of application No. 12/562,622, filed on Sep. 18, 2009, now Pat. No. 8,685,487, which is a continuation of application No. PCT/JP2008/053387, filed on Feb. 27, 2008.

(30) Foreign Application Priority Data

Mar. 20, 2007 (JP) ................................. 2007-072803

(51) Int. Cl.
  *A61L 33/00* (2006.01)
  *B05D 3/00* (2006.01)
  (Continued)

(52) U.S. Cl.
  CPC . *A61F 2/91* (2013.01); *B05D 1/002* (2013.01); *B05D 1/26* (2013.01); *B05D 1/32* (2013.01)

(58) Field of Classification Search
  CPC ............. A61F 2/91; A61F 2/82; B05D 1/002; B05D 1/26
  USPC .......... 427/2.24, 2.25; 118/668, 669, 680, 323
  See application file for complete search history.

(56) References Cited

U.S. PATENT DOCUMENTS 6,153,252 A 11/2000 Hossainy et al.
6,676,987 B2 * 1/2004 Zhong et al. .................. 427/2.24
(Continued)

FOREIGN PATENT DOCUMENTS

CN 1671427 A 9/2005
EP 1325758 A2 7/2003
(Continued)

OTHER PUBLICATIONS

Office Action (Notice of Final Rejection) issued on Jun. 27, 2014, by the Korean Patent Office in corresponding Korean Patent Application No. 10-2009-7019472 and an English translation of the Office Action. (5 pages).

(Continued)

*Primary Examiner* — Cachet Sellman
(74) *Attorney, Agent, or Firm* — Buchanan Ingersoll & Rooney PC

(57) ABSTRACT

A coating method and a coating apparatus are used to apply coating material to struts of a medical device (e.g., stent) which bound openings. The method involves optically scanning the medical device to produce position information identifying positions of the struts, using the position information to calculate a predetermined position, setting an applying manner to apply the coating material based on the predetermined position, setting an applying path accommodating the applying manner, and relatively moving the medical device and an applicator head along the applying route and path while dispensing the coating material from the applicator head and applying the coating material to the struts.

13 Claims, 7 Drawing Sheets

(51) Int. Cl.
*B05C 11/02* (2006.01)
*A61F 2/91* (2013.01)
*B05D 1/00* (2006.01)
*B05D 1/26* (2006.01)
*B05D 1/32* (2006.01)

(56) References Cited

U.S. PATENT DOCUMENTS

| | | | |
|---|---|---|---|
| 6,682,771 | B2 | 1/2004 | Zhong et al. |
| 7,048,962 | B2 | 5/2006 | Shekalim et al. |
| 2002/0085054 | A1 | 7/2002 | Tokie |
| 2003/0003221 | A1 | 1/2003 | Zhong et al. |
| 2003/0139801 | A1* | 7/2003 | Sirhan et al. .......... 623/1.15 |
| 2004/0018296 | A1* | 1/2004 | Castro et al. .......... 427/2.25 |
| 2005/0261764 | A1 | 11/2005 | Pacetti et al. |
| 2007/0196423 | A1* | 8/2007 | Ruane et al. .......... 424/423 |

FOREIGN PATENT DOCUMENTS

| | | |
|---|---|---|
| JP | 2000-51367 A | 2/2000 |
| JP | 2003-205037 A | 7/2003 |
| JP | 2004-516935 A | 6/2004 |
| JP | 2005-514988 A | 5/2005 |
| JP | 2005-534399 A | 11/2005 |
| WO | 01/91918 A1 | 12/2001 |
| WO | 03/059410 A1 | 7/2003 |
| WO | 2004/012784 A1 | 2/2004 |

OTHER PUBLICATIONS

International Search Report for PCT/JP2008/053387 completed May 1, 2008.
Extended European Search Report issued on Aug. 26, 2011 by the European Patent Office in corresponding European Patent Application No. 08 72 0935.
Chinese Office Action (Notification of the First Office Action) dated Mar. 29, 2012, issued in corresponding Chinese Patent Application No. 2008800004402.1, and an English Translation of Office Action. (11 pages).
Japanese Office Action issued Jul. 2, 2013 by the Japanese Patent Office in Japanese Patent Application No. 2009-505112 and English translation thereof.
Communication pursuant to Article 94(3) EPC issued by the European Patent Office on Jun. 25, 2012, in the corresponding European Application No. 08 720 935.9-1215 (5 pages).
Korean Notice of Preliminary Rejection dated Dec. 23, 2014 for corresponding Application No. 10-2014-7026748.

* cited by examiner

COATING METHOD AND COATING APPARATUS

This application is a continuation of U.S. application Ser. No. 12/562,622, filed on Sep. 18, 2009, now U.S. Pat. No. 8,685,487, which is a continuation of International Application No. PCT/JP2008/053387 filed on Feb. 27, 2008, the entire content of which is incorporated herein by reference. This application is also based on and claims priority under 35 U.S.C. §119(a) with respect to Japanese Application No. 2007-072803 filed on Mar. 20, 2007, the entire content of which is incorporated herein by reference.

TECHNICAL FIELD

The disclosure here generally pertains to medical devices. More specifically, the disclosure here involves coating a medical device such as a stent.

BACKGROUND DISCUSSION

A stent is a kind of medical device and generally speaking is a tube shaped appliance used for medical purposes such as maintaining a state in which a stenosis portion occurring in a blood vessel or other tubular lumen inside a living body is dilated, reinforcing a lumen and the like.

For example, in case of using a stent to maintain the extended/enlarged portion after a percutaneous transluminal coronary angioplasty (PTCA), the re-stenosis ratio is lower compared with that of the case of only the PTCA. However, re-stenosis can occur approximately 20% to 30% of the time. A main cause of the re-stenosis after the stent placement is intimal hyperplasia. Consequently, there has been developed a drug eluting type stent which prevents re-stenosis by coating a stent with a medicine capable of repressing migration and proliferation of a vascular smooth muscle cell, which are the direct cause of the intimal hyperplasia and by eluting the drug at the stent placement region.

The medicine used includes taxol (paclitaxel), mitomycin C, adriamycin, genistein, tyrphostin, cytochalasin, sirolimus (rapamycin) or the like.

When the coating is completed, a coating liquid in which the medicine and a biocompatible polymer are dissolved into a solvent is used and applied on a portion of a stent or on the entire stent such that a predetermined quantity of medicine will exist on the surface of the stent.

Known coating methods which has been employed in the past include a dipping method and a spraying method. The dipping method is a method in which a stent is dipped into a coating liquid, pulled up, dried and solidified so as to form a coating layer on the stent.

However, a stent is formed with a groove or a through hole (hereinafter, referred to as space portion) between linear struts, and so it may happen that a web (a membrane between struts) or a bridge is generated at a space portion caused by the dipping. In the case of a stent used by being extended, there is a fear that such a web or a bridge could exert an influence on the mechanical function of the stent, and a portion of the web or the bridge may be destroyed or peeled away after applying the stent. If this portion was to flow into a peripheral vessel, there is also a fear that blood flow obstruction will occur.

The spraying method is a method in which a coating liquid is sprayed over the outer circumferential surface and/or the inner circumferential surface of a stent while rotating the stent and/or moving the spray nozzle. Drying and solidification are then applied so as to form a coating layer. However, with respect to the sprayed coating liquid, the amount actually attached on the stent as compared to the sprayed amount can be relatively small and so a large amount of coating liquid is wasted. Many of the medicines included in the coating liquid are generally extremely expensive and so wasting the coating liquid can result in a steep rise of the cost of the stent itself. Also, many of the medicines included in the coating liquid are medicines having toxicity and so it is also necessary to strictly carry out safety management during spraying so as not to scatter the medicine by the spray into the environment. The facilities cost will thus also increase.

Consequently, Japanese Unexamined Patent Publication No. 2000-51367 proposes a constitution in which a web or a bridge is not generated at the space portion by relatively moving a spindle (mandrel) holding the stent and the stent after applying a coating liquid on a stent.

In addition, Japanese Unexamined Patent Publication No. 2003-205037 discloses a method in which a principle of an electrode position coating is used and electric charge is applied between spray means and the stent so as to heighten the coating efficiency.

Further, in a method mentioned in Japanese Unexamined Publication No. 2005-514988, a shape pattern of the stent is obtained by a scanning and a coating liquid is applied along this pattern.

However, with respect to the methods disclosed in Japanese Unexamined Patent Publication No. 2000-51367 and Japanese Unexamined Patent Publication No. 2003-205037 mentioned above, nether involves a method in which the coating liquid is applied along the pattern shape of the stent and therefore, it is undeniable that coating liquid will be wasted.

Also, with the method in Japanese Unexamined Publication No. 2005-514988, the coating liquid is applied by using a solenoid and so the amount of the medicinal solution to be coated on the stent cannot be set correctly and there is a problem that the effect of reducing the re-stenosis ratio in case of the PTCA mentioned above or the like is insufficient.

SUMMARY

A coating method and coating apparatus disclosed here are able to avoid formation of a web or a bridge at the space portion of the medical device, yet accurately form a coating layer having a uniform thickness.

According to one aspect, a method of applying coating material to the struts of a medical device having plural spaces each bounded by several of the struts extending continuously involves optically scanning the outer surface of the medical device to produce position information identifying positions of the struts, using the position information to calculate a predetermined position in the width direction of the strut, setting an applying manner to apply the coating material based on the predetermined position, setting an applying path accommodating the applying manner, relatively moving the medical device and an applicator head along the applying path while dispensing the coating material from the applicator head and applying the coating material to the struts.

According to another aspect, a coating apparatus comprises a holder holding a mandrel configured to removably receive a medical device having plural spaces each bounded by struts extending continuously, rotating means connected to the mandrel for rotating the mandrel, an applicator head comprising a dispenser adapted to contain coating material and a nozzle through which coating material in the dispenser is discharged, moving means for effecting relative movement between the applicator head and the holder in two mutually orthogonal directions, first position information obtaining means for scanning an outer surface of the medical device held at the holder and for obtaining X-direction and Y-direction position information in an orthogonal coordinate system about an exterior surface of the strut, and a control unit connected to the holder, the applicator head and the moving means for controlling the holder, the applicator head and the moving means based on the position information obtained by the first position information obtaining means. The applicator head continuously discharges the coating material from the nozzle and applying the coating material on the outer surface of the strut.

The coating material is applied by being pushed out continuously along the strut of the medical device so that a web or a bridge is not susceptible to being formed in the medical device, yet it is possible to quite accurately form a coating layer having a uniform thickness on the strut of the medical device. In addition, waste of the coating material is minimized as the coating material is applied only on portions of the medical device. The method is thus economical and safety management is relatively easy.

When setting an applying route so as to apply the coating material onto all the surface of the struts, the effect of the therapeutic substance is brought out at all the regions of the struts.

When the method involves setting an applying route that includes at least one section in which repetition application is performed and/or or jumping is performed from one point to another point, the applying route can be shortened and a speedy application becomes possible. In addition, on an occasion of setting an applying manner, if the section applied overlappingly is reduced or shortened as much as possible and also if the applying route of applying the coating material onto all the surface of the struts is selected, a predetermined quantity of medicine can be applied relatively rapidly and uniformly.

When the applying path at the straight portion of the strut is set at the center line position in the width direction of the strut, the coating material is not likely to be disengaged from the strut top and the formation of a web or a bridge will be generated.

When the applying path at the curved portion of the strut is set at a position deviated by a predetermined distance in the width direction from the center line position, the coating material is inhibited from being disengaged from the strut top depending on the characteristic of the coating material discharged from the nozzle.

In particular, if the deviation position of the applying path which is located in the curved portion of the strut is set outside the center line of the curved portion of the strut, disengagement of the coating material from the strut top is more reliably inhibited.

Setting the applying path to be at an intersection point of the center axis or center lines of the plurality of struts or in the vicinity of the intersection point in the crossing portion of the strut, the coating material is inhibited from being disengaged from the strut top even if a plurality of coating layers are formed.

Setting the applying paths of the coating layer where the applying has already finished and a next coating layer to be identical allows a plurality of coating layers to be formed extremely smoothly and also rapidly.

When the applying path of a next coating layer is set so as not to overlap the applying path of the coating layer where applying has already finished for at least a portion thereof, the coating material can be applied with a generally uniform thickness without being disengaged from the strut top.

A gap can be provided between the outer circumferential surface of a mandrel adapted to hold the medical device and the inner circumferential surface of the strut of the medical device at least at a point at which coating application is initiated.

The moving speed of the applicator head can be made faster during application of the coating material in a section of the medical device in which it passes a plurality of times compared with that during the section in which it passes single time for a predetermined applying route. The coating thickness is thus more uniform and the applying time is shortened.

Plural kinds of coating materials can be applied so the medicinal effects become additive, physical and mental burdens are reduced for a patient and it becomes extremely advantageous.

The distance between the nozzle and the strut is preferably 1 μm to 100 μm, and the front edge inner diameter of the nozzle is 5 μm to 250 μm. In this way, the applying can be realized without dropping out the coating material from the strut.

The applicator head can include a plurality of nozzles and a plurality of dispensers so the application of the coating material is realized more rapidly.

The coating apparatus can include a second position information obtaining means for measuring position information of Z-direction displacement in the orthogonal coordinate system on the surface of the strut so that the application of the coating material becomes possible corresponding to various struts.

The control unit preferably controls the movement of the applicator head and the nozzle along the applying path set based on the position information obtained by the first position information obtaining means obtaining the position information of the X-direction and the Y-direction in the orthogonal coordinate system and also, such that the distance between the applicator head and the strut is based on the position information of the Z-direction displacement which the second position information obtaining means obtains. The applicator head and other parts of the apparatus can be housed in a chamber for which temperature and humidity are controlled to help facilitate forming a coating layer having a generally uniform thickness.

DETAILED DESCRIPTION

Figure 1:
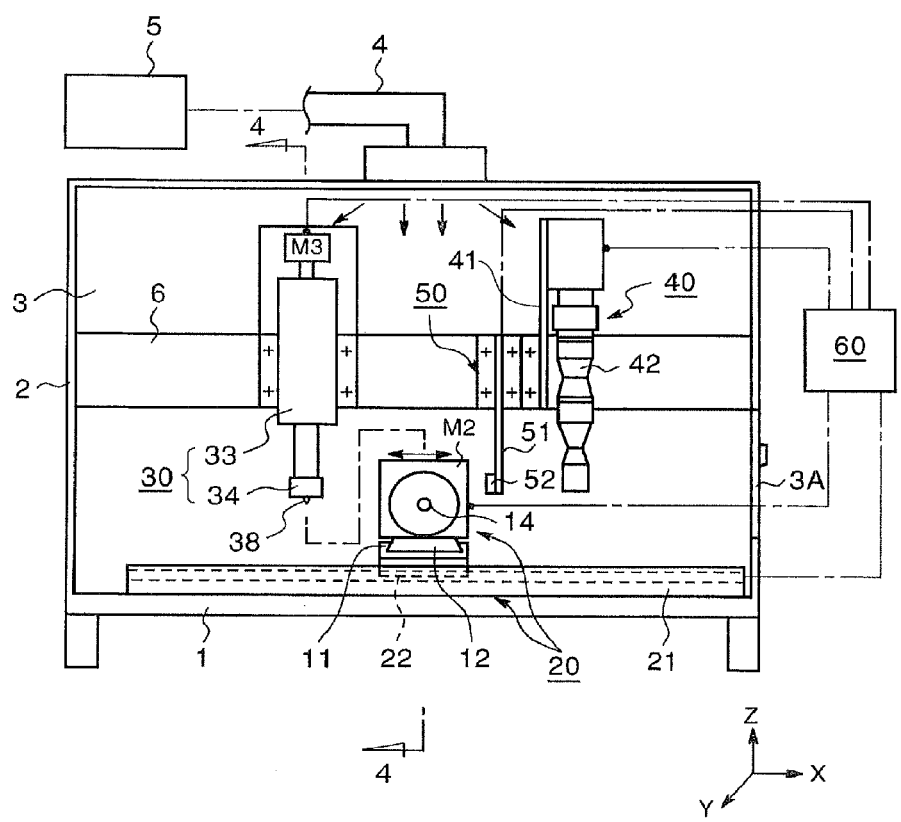
FIG. 1 is a schematic front elevational view of a coating apparatus disclosed here.

Referring the FIG. 1, an example of the coating apparatus disclosed here includes a base 1, a frame 2, supported or mounted on the base 1, and an air-tight chamber 3 inside the frame 2.

The air-tight chamber 3 can be formed by covering the frame 2, provided elevationally on the base 1, from the outer surface or from the outside. This covering can be a transparent synthetic resin covering (plate). A duct 4 is interlinked to the top portion of the air-tight chamber 3 and communicates with the interior of the air-tight chamber 3. Air whose temperature and humidity are controlled is supplied from an air conditioner 5 to the interior of the chamber 3. The apparatus is appropriately configured so that the inside of the chamber 3 is a constant temperature and humidity, and so that drying and solidifying conditions when a coating material C mentioned later is applied on a stent W are always kept constant.

A holder 10 is provided at a lower portion of the inside of the chamber 3. The holder 10 is configured to hold the medical device which in this disclosed embodiment is in the form of a stent W. Also positioned at the lower portion of the inside of the chamber 3 is a moving means 20 operatively connected to the holder 10 to move the holder 10. A support frame 6 laterally bridges the frame 2 (extends between opposite upstanding sides of the frame 2) at an intermediate portion of the interior of the chamber 3. An applicator head 30 which supplies the coating material C on an elongated strut S of the stent W is mounted on the support frame 6 and is positioned at an intermediate portion of the interior of the chamber 3. Also mounted on the frame 6 and positioned at the intermediate portion of the chamber interior are: first position information obtaining means 40 which obtains position information in the X-Y-directions in an orthogonal coordinate system on the surface of the stent W, in other words, on the surface of the strut S; and second position information obtaining means 50 which obtains position information in the Z-direction in the same orthogonal coordinate system.

Positioned outside the chamber 3 is a control unit 60 operatively connected to the holder 10, the moving means 20, the applicator head 30 and both position information obtaining means 40, 50. The control unit 60 controls the holder 10, the moving means 20, the applicator head 30 and the first and second position information obtaining means 40, 50.

However, it is sufficient if there exists at least the holder 10 and the applicator head 30 in the inside of the chamber 3. The first and second position information obtaining means 40, 50 need not necessarily exist in the chamber in which the temperature and humidity are controlled.

Figure 2:
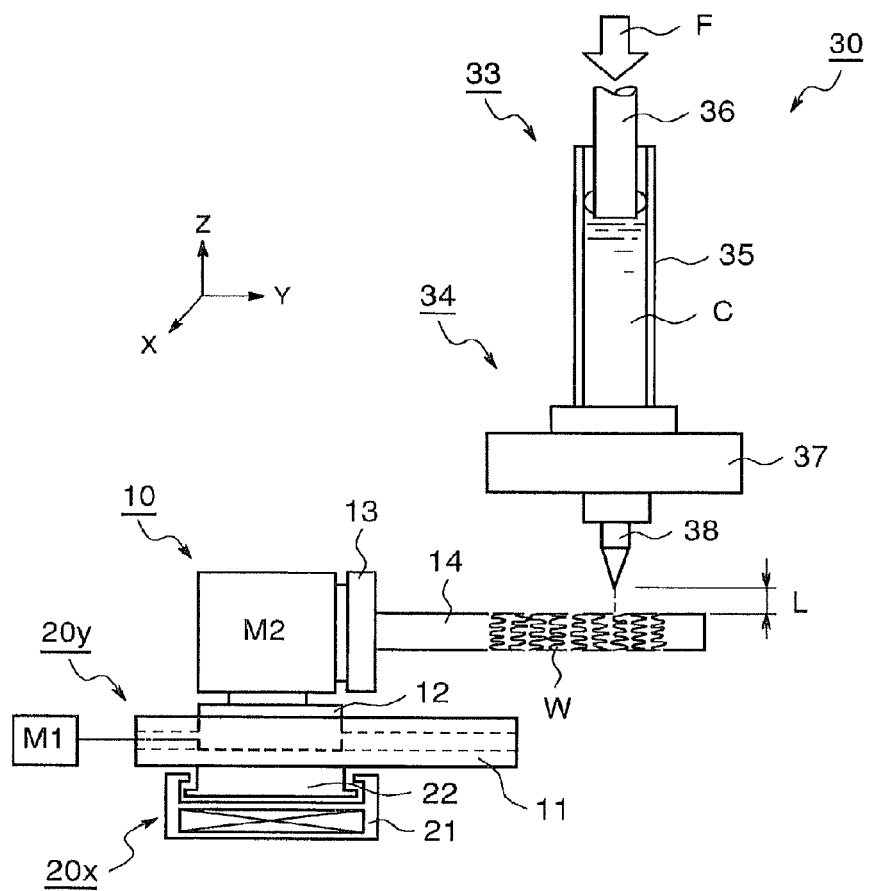
FIG. 2 is a schematic front elevational view of a holder and an applicator head used in the coating method disclosed here.

The holder 10 is moved in the X-Y-directions by the moving means 20. As shown in FIG. 2, first moving means 20x (X-direction moving means or first-direction moving means) can be a linear motor system in which a base plate 11 is mounted on a movable table 22 which is movable along a traveling rail 21. The holder 10 is fixed to a slide portion 12, and the slide portion 12 is slidably mounted on the base plate 11. At the slide portion 12 there is provided, a second moving means 20y (Y-direction moving means or second-direction moving mean) which is composed of a screw-transfer mechanism or the like which is rotated by a motor M1. The slide portion 12 is provided with a motor M2 and a chuck portion 13. The proximal end of a mandrel 14 on which the stent W is detachably positioned is chucked or held at the chuck portion 13 and it is constructed such that it can be rotated rotatably in forward and reverse directions by the motor M2.

The outside diameter of the mandrel 14 is approximately the same as or a little bit larger than the inside diameter of the stent W. The mandrel 14 is exchangeable in conformity with the inside diameter of the stent W. That is, the mandrel 14 can be exchanged for a mandrel 14 with a different diameter as the diameter of the stent changes. There can be prepared mandrels having several different outside diameters. The mandrel (s) is coated with a black coating material to absorb light and heighten a contrast ratio between the mounted strut S of the stent W and space portions O.

Figure 3A:
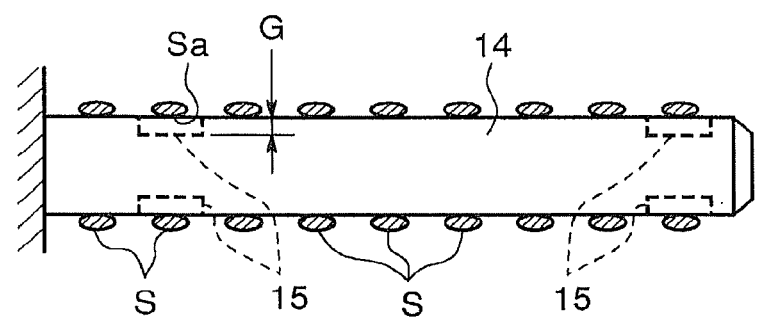
FIG. 3A is an enlarged cross-sectional view of a portion of the holder shown in FIG. 2
Figure 3B:
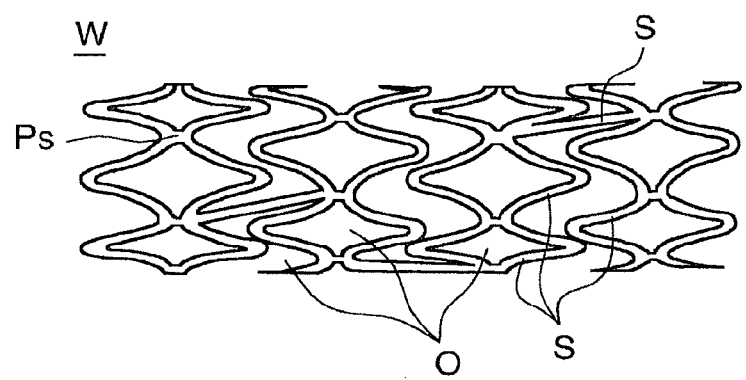
FIG. 3B is a plan view of a portion of a stent shown in FIG. 3A.

Also, as shown in FIG. 3A, the outer circumferential surface of the mandrel 14 is provided with concave portions 15. These concave portions 15 can be annular in shape, meaning they each extend around the entire circumference of the mandrel 14 and are axially spaced apart from one another along the length of the mandrel. Alternatively, the concave portions 15 can be individual spaced-apart recesses or depressions in the surface of the mandrel. With the concave portions 15 formed on the outer circumferential surface of the mandrel 14, a gap G occurs between the outer circumferential surface of the mandrel 14 and the inner circumferential surface Sa of the strut S of the stent W when the stent W is mounted on the mandrel 14. By virtue of this gap G, when the coating material C is applied on the strut S and even if the coating material C runs out to the side surface of the strut S, the coating material C can be inhibited or prevented from turning around a portion between the surface of the mandrel 14 and the inner surface of the stent W. Also, it is possible, without generating a web or a bridge, to form a coating layer having a uniform thickness on the strut S of the stent W. Furthermore, it is possible to avoid also release difficulties that might otherwise arise when releasing the stent W from the mandrel 14. The turning around of the coating material C occurs relatively easily at a starting point from which the coating material C is applied on the strut S, so that it is possible for the concave portion 15 to exist only at a portion corresponding to an application start point shown by "Ps" in FIG. 3B, in other words, only at the under portion of, so-called, an X shape portion (crossing portion of the strut S) which exists in one end region of the strut S. However, it is not limited solely to this as it is also possible to form them widely such that the concave portions 15 exist at the inner circumferential surface of all the struts S other than the both end portions, and it is also possible to form them partially (i.e., to provide the concave portions or recesses 15 at more then just the struts at the end portions, but not at all the struts).

Here, the stent W is a stent generally having a cylindrical shape over its entire length and is composed of bent or curved linear struts S having a predetermined width and space portions O formed between (bounded by) the struts S. Also, the stent is manufactured from a biocompatible and biostable material. For example, possible metal materials which can be used to fabricate the stent include stainless steel, Ni—Ti alloy, tantalum, titan, gold, platinum, inconel, iridium, tungsten or cobalt alloy (including cobalt-chromium-nickel alloy). Examples of high-polymer material which can be used include polytetrafluoroethylene, polyethylene, polypropylene, polyethylene terephthalate or polyamide. Examples of a biodegradable high-polymer material which can be used to fabricate the stent include polylactic acid, polyglycolic acid, polylactide, polyglycolide, polyparadioxanone, trimethylene carbonate, ϵ-caprolactone and the like or a mixture, a copolymer of those above.

Also, the coating material C is a material including at least a solvent, a polymer and a therapeutic substance. It is preferable for a polymer usable as the coating material C to be a material having appropriate adherence with respect to the strut S and having film formability which can follow the deformation (shape/configuration) of the stent W. The polymer can be either biodegradable or non-biodegradable, and it is preferable that the polymer have an excellent biocompatibility characteristics in order to minimize inflammation of a blood vessel wall. Also, in the case of a non-biodegradable polymer, it is preferable to select a polymer controllable such that the therapeutic substance will be eluted over time. In the case of a biodegradable polymer, it is preferable to select a polymer which will be decomposed in an appropriate time period. Examples of a biodegradable polymer which can be used include polylactic acid, polyglycolic acid, poly-butyric acid, poly-hydroxybutyric acid, polyparadioxanone, trimethylene carbonate, ε-caprolactone, poly-malic acid, poly-α-amino acid, collagen, laminin, heparan sulfate, fibronectin, vitronectin, chondroitin sulfate, hyaluronic acid and the like or a mixture, a copolymer of those above.

Examples of a non-biodegradable polymer which can be used include silicone, cellulose-based polymer, polyurethane, polyester, polymethacrylate, polyethylene-oxide, polyvinyl alcohol, polyethylene glycol, polyvinyl pyrrolidone, poly-acrylic acid or the like.

For the therapeutic substance, examples of a medicine which suppresses migration & proliferation of vascular smooth muscle cells and which can be used in the coating include taxol (paclitaxel), actinomycin C, mitomycin C, adriamycin, genistein, tyrphostin, cytochalasin, sirolimus (rapamycin), tacrolimus, everolimus or the like.

It is preferable for the solvent to be a solvent which dissolves a polymer, a therapeutic substance and the like, but it is possible to select a solvent which can disperse those uniformly. Also, it is preferable for the stent W to be provided with wettability and an appropriate vaporization speed, and the stent is preferably selected by achieving a balance therebetween. Preferable solvents include acetone, N-methylpyrrolidone, dimethyl sulfoxide, toluene, xylen, methylene chloride, chloroform, fleon, dioxane, acetic ether, tetrahydrofuran, dimethylformamide, dimethylacetamide or a mixture of those above.

Further, it is also possible to add additive agents aiming for adjustment of the physical characteristic of the polymer film, improvement of adherence with respect to the stent W, viscosity adjustment of the coating solution, oxidation inhibition of the therapeutic substance or the like. Examples of those additives include glycerol, triacetyl glycerine, ethylene glycol, triethylene glycol, polyethylene glycol, polypropylene glycol, propylene glycol, polyalkylene-oxide, sebacic acid ester, citric acid ester, phthalic acid ester or the like.

The coating material C discharged from a nozzle 38, described in more detail below, is deployed on the strut S. The preferable viscosity of the coating material C is 0.1 cp to 10 cp, preferably 1.0 cp to 4.0 cp. When the viscosity is substantially higher than this level, there exists a possibility that a relatively large pressure will be required to discharge or the discharge of the coating material from the relatively thin nozzle 38 will not be possible. When the viscosity is substantially lower than the noted level, the discharged coating material C runs out of the strut S and there may happen a case in which a uniform coating layer cannot be formed.

Figure 4:
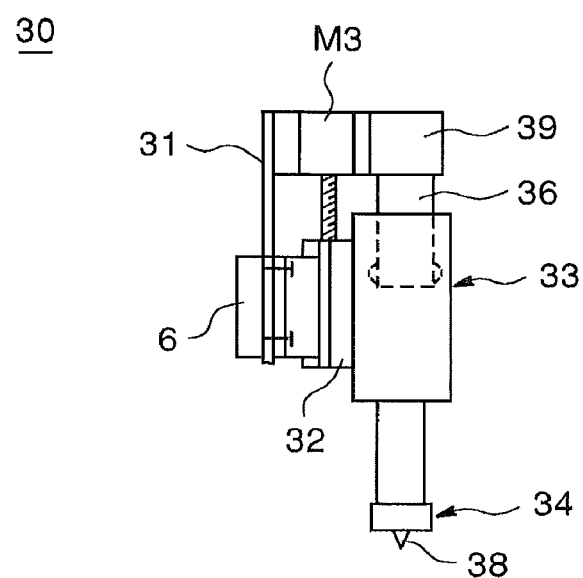
FIG. 4 is a schematic cross-sectional view along the section line 4-4 line in FIG. 1.

The applicator head 30 includes, as shown in FIG. 4, a dispenser 33 composed of, for example, a syringe operation mechanism and a nozzle portion 34 for discharging the coating material C. The dispenser 33 is mounted on a vertical table 32. The vertical table 32 is mounted in the support frame 6 by a bracket 31. The vertical table 32 is moved in the Z-direction by the screw-transfer mechanism or the like driven by a motor M3, and the dispenser 33 gradually discharges the coating material C retained in the inside of the nozzle. As discussed below in more detail, the syringe operation mechanism and the nozzle portion 34 are thus movable in the Z-direction to maintain a constant distance or spacing between the surface of the stent and the nozzle tip during coating application.

The dispenser 33 of this disclosed embodiment includes, as shown in FIG. 2, a cylinder portion 35 having an interior in which the coating material C is retained, a piston portion 36 slidably positioned in the interior of the cylinder portion 35, and a driving unit 39 which presses the piston portion 36 by a predetermined force F. The driving unit can be, for example, a motor, a liquid pressure mechanism or the like.

The nozzle portion 34 comprises a mounting member 37 at the lower end of the cylinder portion 35, and the nozzle 38 which is directed downwardly (hangs down) from the mounting member 37. The nozzle portion thus forms a flow route along which the coating material C flows from the cylinder portion 35 to the nozzle 38.

The outer diameter of the tip of the nozzle 38 is 10 μm to 1000 μm, and the inner diameter of the tip of the nozzle 38 is 1 μm to 500 μm, preferably 5 μm to 250 μm, such that the coating material C having the viscosity mentioned above is able to be pushed out with a predetermined discharge speed. In the case of a nozzle tip having an inner diameter substantially less than 5 μm, the coating material C does not flow out in a sufficiently smooth manner. Also, a large pressure will be required to effect the discharge. In the case of an inner diameter substantially greater than 250 μm, there is a concern that the coating material C cannot be applied substantially smoothly on the top of the stent W which is used presently.

Also, it is preferable for the nozzle 38 (outside surface of the nozzle) to be polished to lessen surface irregularity as much as possible in order to avoid the attachment of the discharged coating material C. Consequently, it is preferable to use, for example, stainless steel, carbon steel, nickel, chromium, glass, aluminum oxide, zirconium oxide, diamond, a mixture of those above or the like, as these materials can be relatively easily processed.

As shown in FIG. 2, the dispenser 33 in this disclosed embodiment is constructed such that it is able to deposit the coating material C on the surface of the strut S while being spaced apart from the stent such that the distance L between the nozzle 38 and the strut S is a predetermined distance and the coating material C will be pushed out continuously without a break from the nozzle 38 and directed to the surface of the strut S. If such a continuous push-out system is employed, uniform application of the coating material C becomes possible with respect to the whole surface of the stent W and also, the continuous push-out system can quantitatively discharge, so that controllability is excellent and quantitative adjustment of the therapeutic substance can be carried out relatively accurately and reliably. Furthermore, in the inside of the chamber which is adjusted for the constant-temperature & constant-humidity, the condition by which the coating material C is dried and solidified is constant, so that production of the stent W on which the coating material C is deposited can be carried out easily and also rapidly.

The distance L between the nozzle 38 and the strut S is preferably 0.1 μm to 200 μm, more preferably 1 μm to 100 μm, as measured along an imaginary continuation of an axis of the nozzle. When the distance L is substantially larger than this distance, a problem might arise in that the coating material C will be interrupted. When the distance L is substantially shorter than the noted distance (i.e., is excessively narrower), a problem can arise in which the coating material C runs out of the surface of the strut.

In the embodiment disclosed here by way of example, the applicator head 30 is a head having one nozzle 38 and one dispenser 33, but it is also possible to employ a head having a plurality of nozzles 38 and a plurality of dispensers 33. Providing a head having a plurality of nozzles 38 and a plurality of dispensers 33 makes it possible to carry out the application of the coating material C in shorter time, thus improving productivity and providing advantages from the standpoint of production cost.

The first position information obtaining means 40 shown in FIG. 1 includes imaging means for obtaining an image. The imaging means (e.g., a camera unit) is mounted in a position-fixed manner on a bracket 41 which is mounted on the support frame 6. More specifically, the first position information obtaining means 40 includes a camera unit 42 and a line sensor unit arranged to extend in the axial direction of the stent W. The camera unit 42 and the line sensor scan the surface of the stent W in synchronization with the rotation of the stent W of the holder 10, obtain an image of the surface of the stent W and communicate it to the control unit 60. As a start position at which the line sensor unit begins to obtain the surface image of the stent W, any position is acceptable, but preferably it is set on, for example, an axial center line corresponding to the application start point Ps mentioned above. The camera unit 42 and the line sensor unit are known features and are thus not discussed in detail here.

As mentioned above, the mandrel 14 is coated with a black coating material to absorb light and to heighten the contrast ratio between the strut S of the mounted stent W and the space portion O and absorb the light. Thus, with respect to the image of the stent surface, the luminance of the strut S is relatively higher and the luminance of the space portion O is relatively lower. Consequently, it is possible for the control unit 60 to distinguish between the strut S and the space portion O, and to output the coordinates of the strut S, that is to output the X-Y-directions position information of the strut S by binarizing the obtained surface image of the stent W depending on appropriate luminance. Further, the control unit 60 calculates the coordinates of an orbit or movement path along the center line of the strut S (the center of the strut relative to the width-wise direction) based on the obtained X-Y-direction position information (X-Y coordinates of the strut S), and the obtained data of the center movement path is stored in the memory of the control unit 60. In the case of applying the coating material C, the coating material C should be applied in a manner inhibiting or preventing the coating material from being disengaged from, or misapplied to, the strut S and also for this reason, it is important that the center of the strut S is specified.

The second position information obtaining means 50 is, as shown in FIG. 1, comprised of a displacement measuring means of the Z-direction for measuring displacement in the Z-direction. The Z-direction displacement measuring means is mounted in a position-fixed manner on the lower end of a bracket 51 mounted on the support frame 6. In this disclosed embodiment, the Z-direction displacement measuring means is comprised of a laser displacement sensor 52, a so-called vertical sensor, and measures displacement or the position of the strut S in the Z-direction.

The strut S is a strut whose surface is not smooth in a precise sense and has irregularity. In order to apply the coating material C quantitatively precisely on the strut having such irregularity, the distal end of the nozzle 38 should desirably be moved so it is parallel with the surface of the strut S precisely (i.e., so the nozzle 38 follows the configuration or terrain of the strut S) and a predetermined amount of coating material C is applied. Consequently, in this embodiment disclosed by way of example, by using the laser displacement sensor 52, the position information of the strut S that is obtained is started from a predetermined position of the stent W, for example from the application start point Ps. The laser displacement sensor 52 is scanned along the orbit or path of movement by rotating the mandrel 14 in the forward and reverse direction, and moving the holder 10 in the Y-direction because the laser sensor 52 is fixed in the support frame 6 in this embodiment. Displacement data is thus collected. The displacement data corresponds to or represents the coordinates of a movement path (orbit) along the center line of the strut(s). The obtained displacement data is communicated to the control unit 60 and stored in the memory.

In the embodiment described above, the second position information obtaining means 50 is provided as a single laser displacement sensor 52. However, a plurality of the laser displacement sensors 52 can be provided, and in such an alternative arrangement, the position information can be realized more rapidly.

The control unit 60 includes a processor, a monitor, a keyboard and the like. Based on the position information obtained from the position information obtaining means 40, 50, the control unit 60 determines the setting of an applying manner by which the coating material is applied and an applying path along which the applicator head 30 applies the coating material C on the strut S of the stent W. Also, the control unit 60 controls the rotation of the mandrel 14 in the holder 10, the movement of the moving means 20, the discharge amount of the coating material C discharged from the applicator head 30, the scanning of the imaging means and of the vertical sensor and the like.

Here, an applying manner refers to an applying route in a case in which the application is executed along the strut S of the stent W. It is preferable for the applying route to be a route which does not have a section in which repetitive application occurs and which can apply the coating to the surface of the strut S continuously. However, in the case of a stent W having struts S intersecting in a complicated manner, it may be difficult to set an applying route having no section in which the repetitive application occurs. In such a case, there may be provided a section in which the repetition application occurs or there may be provided a section in which jumping is done from a certain point on the strut S to another point. In this manner, the applying route can be shortened by providing for a portion with a section of repetition application or a section of jumping. Also, in a section of repetitive application (i.e., a section of a stent or strut in which the coating is applied more than once), the medicine can be applied on all the surfaces of the stent W uniformly by setting the speed to be faster in the section of repetitive application than the moving speed during the section where the coating is applied a single time, and it is possible to sufficiently exert an effect of reducing a re-stenosis ratio in the case of PTCA or the like.

Also, on an occasion of the determination of the applying path, it is preferable to implement various kinds of measures such as described below.

Figure 5:
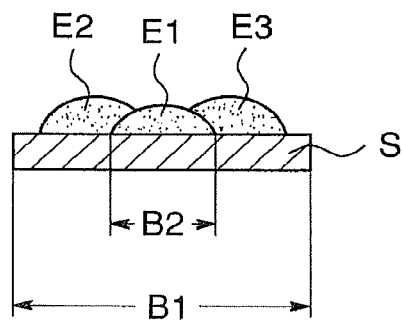
FIG. 5 is a cross-sectional view of a stent showing the applying state of a plurality of coating layers.

(1) In case of applying the coating material C on the strut S of the stent W, it is preferable, at a straight portion of the strut S, to set the applying path to be an orbit or movement path passing along the axial center-line of the strut S. However, at a curved portion of the strut S, it is preferable to set a movement path or orbit which is deviated by a predetermined distance or length from the axial center-line in the width-wise direction of the strut S as the applying path. The coating material C is a liquid and is applied on the surface of the strut S such that it is raised by surface tension. Even if this is dried and solidified, a coating layer having an arc-shaped (dome-shaped) cross-section is formed. Accordingly, when the application is executed a plurality of times (i.e., when the applying route is executed plural times), it becomes a state of being raised in an arc-shape and is not preferable. Consequently, as shown in FIG. 5, it is preferable for a coating layer E2 at the second time to be applied along an applying path that is deviated by a predetermined distance from the coating layer E1 applied to the strut S the first time. It is also preferable for a coating layer E3 at the third time to be applied along an applying path that is different from the applying paths of the first and second times. It is preferable for this amount of deviation to bet determined by taking into consideration a width B1 of the strut S and a width B2 of the coating layer E.

Figure 6:
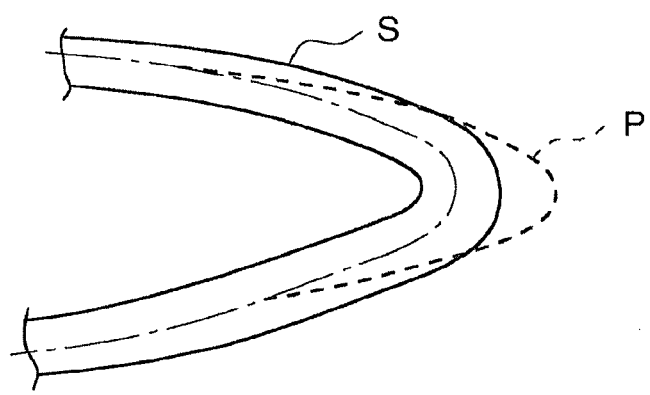
FIG. 6 is a plan view of the applying path of a curved portion.

(2) In determining the applying path, it is preferable for the applying paths to be different in the linear-shaped strut portion and in the curved strut portion. At the linear shaped strut portion, it is generally adequate if the movement path is along the center of the strut S in the width direction of the strut S. However, at the curved strut portion, if the applying path coincides with the center line of the strut S in the width direction of the strut S, the application of the coating material C discharged from the applicator head 30 may be affected by the viscosity of the coating material, the falling speed from the nozzle, or the like, and so the path along which the coating material is applied may not follow the moving path of the applicator head 30. Accordingly, in this embodiment, as shown in FIG. 6, a curved line P (dotted line) passing outside the curved line (dashed-dotted line) passing through the center line of the curved portion of the strut S is set as the applying path.

Here, the applying path P shown by the dotted line extends outwardly to the outside portion of the strut S, and this is based on knowledge that when the coating material C applied on the strut S by being pushed out continuously, the coating material C can be prevented more reliably from being disengaged from the strut S (i.e., from being misapplied or not applied to the strut) depending on the characteristic of the coating material C.

(3) At the crossing portion of the strut S, it is preferable for an intersection point of a center line of plural struts S or the vicinity of the intersection point thereof to be the applying path. At the portion at which the struts S intersect, the applying path P will also be intersected, so that if the intersection point of a center axis line of the struts S or the vicinity of the intersection point is set to be the applying path, it is possible to inhibit or prevent running off of the coating material C which is preferable.

Next, a coating method is explained with reference to FIG. 7 and FIG. 8 which are flowcharts illustrating aspects of the coating method using the apparatus described above.

<Preparation Process>

First, upon starting the coating, the air conditioner 5 is activated and the inside of the chamber 3 is conditioned so it is a constant temperature and constant humidity. Then, at the support frame 6, there is set the applicator head 30, including the syringe operation mechanism 33 and the nozzle portion 34 including the nozzle 38 having an inside diameter corresponding to the width of B1 of the strut S and the coating material C in the cylinder portion 35.

The stent W is attached or mounted on the mandrel 14 and the mandrel 14 is mounted on the chuck portion 13 of the holder 10 which is positioned at a standby position. At that time, the application start point Ps of the strut S is set so as to positioned over the concave portion 15 of the mandrel 14. Here, in the case of having the moving means 20 at the lower portion of the chamber 3, as shown in FIG. 1, the standby position is in the vicinity of an entrance portion 3A of the chamber 3.

<Imaging Process>

Figure 7:
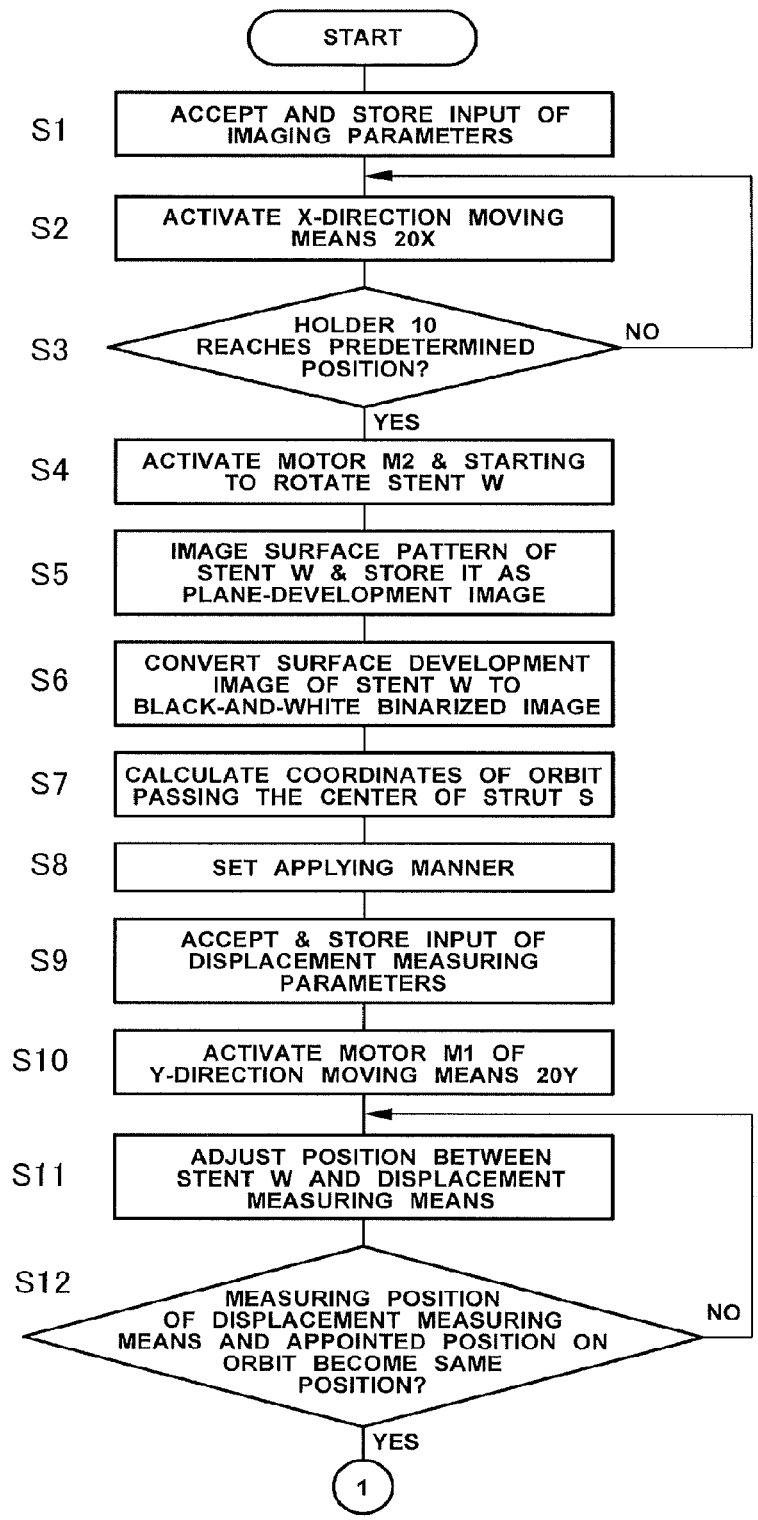
FIG. 7 is a flowchart illustrating aspects of the coating method disclosed here.
Figure 8:
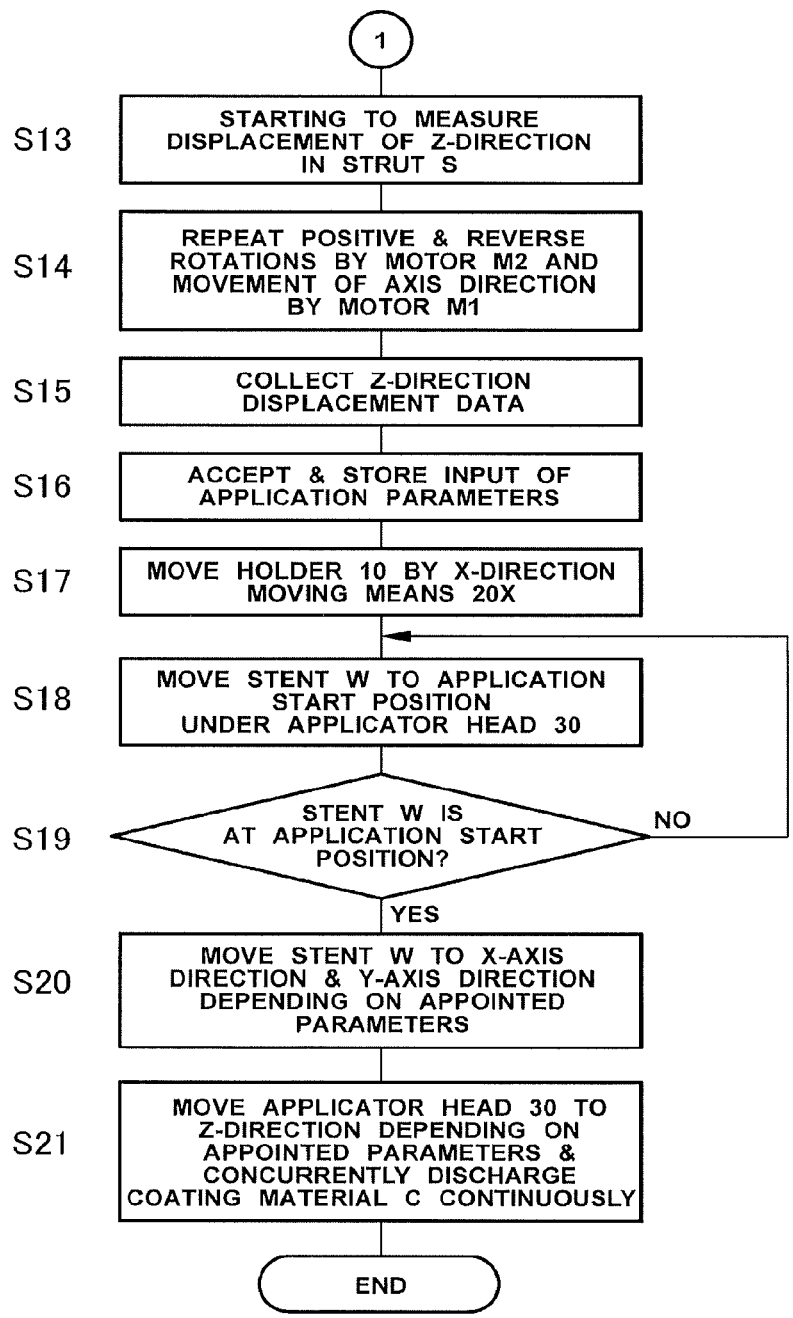
FIG. 8 is a flowchart illustrating other aspects of the coating method disclosed here.

The control unit 60 accepts input in the form of imaging parameters, and the inputted imaging parameters are stored in a storage device (S1 in FIG. 7). The imaging parameters are, for example, inputted from a keyboard by an operator. The imaging parameters include a rotation speed of the mandrel 14, the number of imaging lines, an imaging line width and an operation speed when imaging.

The control unit 60 provides instructions to start imaging after storing the inputted imaging parameters. Concurrently, the X-direction moving means 20x is activated (S2 in FIG. 7). When the X-direction moving means 20x is activated, the holder 10 moves from the standby position under the first position information obtaining means 40 by way of the traveling rail 21. The control unit 60 confirms that the holder 10 reached the predetermined position (S3 in FIG. 7) and if the holder 10 reached the predetermined position, it activates the motor M2 of the holder 10 and starts the rotation of the stent W (S4 in FIG. 7).

The line sensor of the first position information obtaining means 40 starts the imaging based on the imaging start instruction, scans the surface of the stent W relatively, because the stent W is rotating, and images the surface pattern of the stent W (S5 in FIG. 7). The imaged picture is stored in the storage device (for example, memory, hard disk or the like) of the control unit 60 as a plan view development image. In addition, it is also possible to employ an arrangement in which the imaged picture is outputted to a monitor so an operator is able to view or confirm the imaged picture by watching the monitor.

With respect to the surface image of the stent W, the luminance of the strut S is relatively high and the luminance of the space portion O is relatively low. The control unit 60 converts the stent surface image to a black-and-white binarized image by setting a certain luminance as a boundary (S6 in FIG. 7), and calculates the coordinates of the movement path or orbit along the center (center line) of the strut S by a thinning processing of the width of the strut S(S7 in FIG. 7). This thinning processing simply refers to processing that converts the pattern image of the strut S into a linear image, for example a linear image of one pixel in width.

<Setting Process of Applying Manner>

At S8 in FIG. 7, judging the surface image of the stent W obtained by the process and taking into account any perceived necessities (e.g., judging whether or not it is possible to trace the applying route by a single stroke), and considering the position of any section(s) in which repetition application or jumping may be performed, the system sets the applying manner so that all surfaces of the strut S are applied or coated with the coating material during the coating application. The applying manner involves determining for example, whether or not the applying route of the nozzle will include any section(s) of repetition application and/or jumping. The applying route is preferably set such that the section(s) in which the repetition application is done and the section(s) in which the jumping is done are reduced or shortened as much as possible. In the event the applying route includes a repetitive section, the applying manner can also include the speed of the nozzle when moving along the repetitive section of the applying route.

<Displacement Measurement Process of Z-Direction>

Next, the control unit 60 accepts input of displacement measuring parameters of the second position information obtaining means 50 which is the Z-direction displacement measuring means and stores such parameters (S9 in FIG. 7). These displacement measuring parameters are also inputted by an operator. The displacement measuring parameters include data (coordinates) of the measuring start position, the measuring direction, the direction at the branch point, the measuring speed and the measurement point interval. The displacement measuring parameters set the measurement method of the second position information obtaining means 50. These parameters can be, for example, inputted at the keyboard by the operator before the Z-direction displacement measurement. The Z-direction displacement measuring means 50 works or operates according to these parameters.

The control unit 60 activates the motor M1 of the Y-direction moving means 20y after storing the displacement measuring parameters (S10 in FIG. 7). At that time, if necessary while observing by way of a video camera and a monitor, the stent W and the measuring position of the displacement measuring means are adjusted such that the actual measurement start point of the Z-direction displacement measuring means agrees with the start point on the strut S specified by parameters on the monitor (S11 in FIG. 7).

Once this adjustment results in the actual measuring position and the specified position being the same position (confirmation of coincidence of these two positions can be inputted by the operator to the control unit 60 (S12 in FIG. 7: Yes)), the control unit 60 instructs the second position information obtaining means 50 on the start of the measurement of the Z-direction displacement in the strut S(S13 in FIG. 7). Concurrently, the control unit 60 controls the motor M2 to repeatedly rotate in the forward and reverse rotations (clockwise and counterclockwise rotations), and controls the motor M1 to repeatedly move in the axial direction (Y-direction). Thus, the stent W repeatedly rotates and moves in the axial direction or Y-direction (S14 in FIG. 7).

Thus, the second position information obtaining means 50 moves along a movement path that follows the center line of the strut S, and the control unit 60 collects the Z-direction displacement data (S15 in FIG. 7). This displacement data are stored in the storage device of the control unit 60 together with the coordinates of the movement path along the center line. This Z-direction displacement data indicates the distance between the tip of the applicator head and the surface of the strut S (stent), and this information fed to the control unit 60 allows the control unit to effect appropriate control to maintain a constant distance between the tip of the applicator head and the surface of the strut S (stent) during application of the coating material.

<Applying Process>

The control unit 60 accepts an input of application parameters, and stores this input (S16 in FIG. 7). Application parameters are also input by an operator. The application parameters include data of the application start position, the application (applying) direction, the direction at the intersection, setting of the movement path adjustment section, the deviated length of the movement path, the applying speed, the discharge speed of the coating material C, the height of the applicator head, the number of applications (number of layers) and the selection of the applicator heads. Application parameters involving the direction at the intersection include parameters defining the direction in which the nozzle moves when encountering an intersection such as Ps in FIG. 3B where there are multiple direction of movement. Application parameters involving the setting of the movement adjustment section include setting the applying path to deviate from the strut center line as generally indicated by the dotted line P in FIG. 6. Application parameters involving the deviated length of the movement path include setting the amount of deviation of the movement path from the strut center line. Since the application parameters which are inputted and stored at S16 include, for example, data about the application start position, the application (applying) direction, the direction at the intersection, setting of the movement path adjustment section, the deviated length, of the movement path, the applying speed, the discharge speed of the coating material C, the height of the applicator head, the number of applications (number of layers), and the selection of the applicator heads, the applying path is set at S16. That is, S16 constitutes the setting of the applying path which accommodates the applying manner.

The control unit 60 instructs the application start (start of coating material application) after storing the application parameters. Concurrently, the control unit 60 instructs the movement of the holder 10 by the X-direction moving means 20x (S17 in FIG. 7). Thus, the stent W is moved to the application start position under the applicator head 30 (S18 in FIG. 7). Once the stent W reaches the application start position under the applicator head 30 (S19 in FIG. 7: Yes), the control unit provides instruction to the motor M2 to perform the positive and reverse rotations and provides instruction to the motor M1 to effect movement in the axial direction so that the stent W is moved in the X-axis direction and in the Y-axis direction depending on the appointed parameters according to the positive and reverse rotations by the motor M2 and according to the axial movement by the motor M1 (S20 in FIG. 7). During this time, the coating material is applied to the stent struts.

Thus, the stent W is moved in the X-axis direction and the Y-axis direction according to the applying path previously determined (appointed parameters), the applicator head 30 is moved in the Z-direction according to displacement data (appointed parameters) received from the second position information obtaining means 50, and the coating material C is discharged from the applicator head 2 continuously. Thus, the applicator head 2 applies the coating material C moving along the predetermined applying route and path.

During the application of the coating, the space between the distal end of the nozzle 38 and the stent W is in a state of being filled by the coating material C, so that the coating material C is discharged by a fixed amount and the amount of the therapeutic substance on the stent W is also reliably set to be a predetermined value. Furthermore, the web and the bridge are not generated between the struts S, and the coating layer E can be formed extremely accurately.

When the coating is completed, the holder 10 is moved to the standby position by the X-direction moving means 20x, the mandrel 14 is removed from the holder 10 and is taken outside the chamber 3, and the stent W is released or taken off the mandrel 14.

The disclosed method and apparatus here are not limited to the embodiments disclosed by way of example above. Various modifications are possible in the technical idea of the disclosure here, depending on a person skilled in the art. For example, the embodiments described above relate to a case in which one kind of coating material C is applied, but depending on the product, the situation and the like, it is also possible to use plural kinds of coating materials. In case of applying a plurality of coating materials C, a plurality of syringes, nozzles and syringe operation mechanisms can be employed, and the coatings are applied by changing-over them sequentially. The sequential changeover of these syringes, operation mechanisms and the like is controlled by the control unit 60. Here, the different coating material C means the polymer is different or the polymer is the same and the amount thereof is different; the therapeutic substance is different or the amount of the therapeutic substance is different; or the solvent is different. In this manner, if plural kinds of coating materials are used, the medicinal effects become additive and it becomes extremely advantageous in cases such as a case in which physical and mental burdens for a patient are reduced or the like.

Also, in the disclosed embodiments, the holder 10 is moved by the first and second moving means 20x, 20y and the applicator head 30 and the first and second position information obtaining means 40, 50 are fixed. However, it may not always be necessary to employ a construction in which only the holder 10 is always moved and other parts must be fixed. It is possible for these movements to be relative and thus, it is enough if predetermined moving means is installed suitably.

Further, also with respect to the movement directions of the holder 10, the applicator head 30 and the first and second position information obtaining means 40, 50, it is not necessary to always employ a construction in which the applicator head 30 and the holder 10 are relatively moved in two directions orthogonal to each other in the horizontal surface or in which the movement is executed in the vertical direction relatively. It is also possible to select the most suitable condition depending on the shape or the like of the stent W.

INVENTIVE EXAMPLE 1

For the stent W, there was used the following stent and the coating is executed.

Stent W: Inside Diameter of 1.7 mm, Thickness of 150 μm, Full Length of 30 mm

Width of Strut S (minimum): 107 μm

Radius of Curvature of Strut S (minimum): R=0.1 mm

The pattern of strut S is a pattern obtained by connecting rings composed of waveforms with linear shaped links.

The material of the stent W is stainless steel.

Viscosity of Coating Material C, 2.5 cp (20° C.)

Discharge Speed of Coating Material C, 0.0067 μl/sec

Adjustment Deviated Length of Orbit of Curved Portion
: 40 μm in Y-direction (Stent Circumferential Direction)
: 60 μm in X-direction (Stent Long Axis Direction)

Applying Speed on Orbit Passing the Center: 2.4 mm/sec

Applying Speed on Orbit Deviated from the Center: 3.3 mm/sec

Applying Speed in Section of Repetition Application: 4.8 mm/sec

Inner Diameter of Tip of Nozzle 38: 43 μm

Outer Diameter of Tip of Nozzle 38: 200 μm

Distance (L) between Stent W and Nozzle 38: 40 μm

Number of Applications (Number of Layers): 10 Layers

The manner of applying or the applying route was selected such that there was provided a section in which the repetition application occurred at a portion of the applying route, but there was no section in which jumping occurred.

The average thickness of the coating layer of the stent of the inventive example 1 was 40 μm, and the coating could be realized without the web, the bridge and running out to the stent side surface. Average thickness refers to the thickness determined by measuring the thickness at plural locations (e.g., three), adding together the measured thicknesses, and dividing by the number of measured locations.

INVENTIVE EXAMPLE 2

Next, with respect to the stent W, the following stent was used and the coating was carried out.

Stent W: Inside Diameter of 1.7 mm, Thickness of 150 μm, Full length of 30 mm

Width of Strut S (minimum): 104 μm

Radius of Curvature of Strut S (minimum) R=0.07 mm

The pattern of the strut S is obtained by connecting rings composed of waveforms with linear shaped links.

The material of the stent W is stainless steel.

Viscosity of Coating Material C, 2.5 cp (20° C.)

Discharge Speed of Coating Material C, 0.0056 μl/sec

Adjustment Deviated Length of Orbit of Curved Portion
: 32 μm in Y-direction (Stent Circumferential Direction)
: 52 μm in X-direction (Stent Long Axis Direction)

Applying Speed on Orbit Passing the Center: 4.4 mm/sec

Applying Speed on Orbit Deviated from the Center: 5.7 mm/sec

Applying Speed in Section of Repetition Application: 8.8 mm/sec

Inner Diameter of Tip of Nozzle 38: 43 μm

Outer Diameter of Tip of Nozzle 38: 200 μm

Distance (L) between Stent W and Nozzle 38: 40 μm

Number of Applications (Number of layers): 10 layers

The manner of applying or the applying route was selected such that there was provided a section in which the repetition application occurred at a portion of the applying route, but there was no section in which jumping occurred.

The average thickness of the coating layer of the stent of the inventive example 2 was 40 μm and the coating could be realized without the web, the bridge and running out to the stent side surface.

With the coating method and apparatus here, it is possible to reduce the re-stenosis ratio of the dilation portion drastically after the percutaneous transluminal coronary angioplasty (PTCA).

The detailed description above describes preferred embodiments of the coating method and apparatus disclosed here with reference to the accompanying drawings. However, it is to be understood that the invention is not limited to those precise embodiments described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

The invention claimed is:

1. A method of applying a coating material to struts of a medical device having plural spaces each bounded by several of the struts extending continuously, the coating method comprising:

optically scanning an outer surface of the medical device to produce position information identifying positions of the struts;

using the position information to calculate a predetermined position in a width direction of the strut;

setting an applying manner to apply the coating material based on the predetermined position;

setting an applying path accommodating the applying manner; and relatively moving the medical device and an applicator head along the applying path while dispensing the coating material from the applicator head and applying the coating material to the struts;

wherein the struts each possess a center line, and the setting of the applying path comprises setting the applying path in a curved portion of each of the struts so that the applying path deviates from a center line of each of said struts in a width-wise direction of the strut, without crossing the center line, and extending from the curved portion of the strut in the width-wise direction.

2. The method according to claim 1, wherein the setting of the applying manner comprises setting an applying route to apply the coating material onto all the struts of the medical device.

3. The method according to claim 1, wherein the setting of the applying manner sets an applying route to include either a section in which repetitive application of the coating material to one portion of the medical device is performed or a section in which jumping is performed during application of the coating from one point on the medical device to another point.

4. The method according to claim 1, wherein the struts each possess a center line, and the setting of the applying path comprises setting the applying path in a straight portion of the strut so that the applying path is the same as a center line of each of said struts in a width-wise direction of the strut.

5. The method according to claim 1, wherein the setting of the applying path comprises setting the applying path at an intersection point of center lines of a plurality of the struts or a vicinity of the intersection point in a crossing portion of the struts.

6. The method according to claim 1, wherein the setting of the applying path comprises setting the applying path of a second layer of the coating material to be identical to the applying path of a first layer of the coating material applied before the second layer.

7. The method according to claim 1, wherein the setting of the applying path comprises setting the applying path of a second layer of the coating material applied to at least one strut so the second layer of the coating material does not overlap a first layer of the coating material previously applied to the one strut.

8. The method according to claim 1, wherein the medical device is held on a mandrel, and the applying of the coating material forms a gap between an outer circumferential surface of the mandrel and an inner circumferential surface of at least one of struts of the medical device at a point initiating application of the coating material.

9. The method according to claim 1, wherein the applying of the coating material comprises moving the applicator head faster while applying the coating material to a strut in a section of the medical device in which the applicator head passes a plurality of times compared to when applying the coating material to a strut in a different section of the medical device in which the applicator head passes no more than a single time.

10. The method according to claim 1, wherein the applying of the coating material comprises applying plural different kinds of coating materials.

11. The method according to claim 1, wherein the coating material is dispensed from the applicator head by way of a nozzle, a tip end of the nozzle being spaced from the strut by 1 µm to 100 µm as measured along an imaginary continuation of an axis of the nozzle.

12. The method according to claim 1, wherein the coating material is retained in a dispenser and includes at least a solvent, a polymer and a therapeutic substance.

13. The method according to claim 1, wherein the curved portion of each of the struts defines an interior area between linear-shaped strut portions, the applying path extending away from the curved portion of the strut in the width-wise direction and through the interior area.

* * * * *